United States Patent
Cabezas

(10) Patent No.: US 7,622,295 B2
(45) Date of Patent: Nov. 24, 2009

(54) MOLECULAR MICROARRAYS AND HELICAL PEPTIDES

(76) Inventor: Edelmira Cabezas, 12595 Ruette Alliante, Apt. 146, San Diego, CA (US) 92130

( * ) Notice: Subject to any disclaimer, the term of this patent is extended or adjusted under 35 U.S.C. 154(b) by 0 days.

(21) Appl. No.: 11/641,244

(22) Filed: Dec. 19, 2006

(65) Prior Publication Data

US 2008/0145862 A1    Jun. 19, 2008

(51) Int. Cl.
*C12M 3/00* (2006.01)
(52) U.S. Cl. .................................. 435/287.2
(58) Field of Classification Search ........... 435/287.2, 435/7.92; 436/518
See application file for complete search history.

(56) References Cited

U.S. PATENT DOCUMENTS

| | | | |
|---|---|---|---|
| 3,767,398 A | 10/1973 | Morgan | |
| 5,143,854 A | 9/1992 | Pirrung et al. | |
| 5,405,783 A | 4/1995 | Pirrung et al. | |
| 6,121,048 A | 9/2000 | Zaffaroni et al. | |
| 6,239,273 B1 | 5/2001 | Pease et al. | |
| 6,379,895 B1 | 4/2002 | Fodor et al. | |
| 6,406,844 B1 | 6/2002 | Pirrung et al. | |
| 6,416,952 B1 | 7/2002 | Pirrung et al. | |
| 6,444,111 B1 | 9/2002 | Montgomery | |
| 6,506,558 B1 | 1/2003 | Fodor et al. | |
| 6,515,039 B1 | 2/2003 | Ulbricht et al. | |
| 6,566,495 B1 | 5/2003 | Fodor et al. | |
| 6,630,308 B2 | 10/2003 | Stryer et al. | |
| 6,750,963 B2 * | 6/2004 | Sampas | 356/318 |
| 6,770,436 B1 | 8/2004 | Beecher et al. | |
| 6,819,843 B1 | 11/2004 | Braun et al. | |
| 6,919,181 B2 | 7/2005 | Hargreaves | |
| 6,919,211 B1 | 7/2005 | Fodor et al. | |
| 2002/0151473 A1 * | 10/2002 | Braisted et al. | 514/9 |
| 2004/0198637 A1 | 10/2004 | Schultz et al. | |
| 2005/0026202 A1 | 2/2005 | Edman et al. | |

FOREIGN PATENT DOCUMENTS

| | | |
|---|---|---|
| EP | 1288664 A1 | 3/2003 |
| EP | 1384504 A2 | 1/2004 |
| WO | WO-97/39151 | 10/1997 |
| WO | WO-00/33804 | 6/2000 |
| WO | WO-2006105037 A2 | 10/2006 |

OTHER PUBLICATIONS

PCT International Search Report (dated May 25, 2007), International Application No. PCT/US2006/047854—International Filing Date Dec. 15, 2006, (10 pages).
PCT International Search Report (dated Mar. 20, 2008), International Application No. PCT/US2007/022287—International Filing Date Oct. 18, 2007 [Atty. Ref. No. 42P23055PCT], (13 pages).
Fodor, Stephen P., et al., "Light-Directed, Spatially Addressable Parallel Chemical Synthesis", Science vol. 251, US American Association for the Advancement of Science, Washington, DC, XP000486899, (Feb. 15, 1991), (pp. 767-773).
McGall, Glenn, et al., "Light-Directed Synthesis of High-Density Oligonucleotide Arrays Using Semiconductor Photoresists", Proc. Natl. Acad. Sci. USA, vol. 93, Nov. 1996, Applied Physical Sciences, (pp. 13555-13560).
Jean Philippe Pellois, et al., "Individually Addressable Parallel Peptide Synthesis on Microchips", Nature biotechnology, vol. 20, Sep. 2002 (pp. 922-926).
C. Grant Wilson, et al., "Approaches to the Design of Radiation-Sensitive Polymeric Imaging Systems with Improved Sensitivity and Resolution", J. Electrochem. Soc.: Solid-State Science and Technology, vol. 133, No. 1, Jan. 1986 (pp. 181-187).
Masamitsu Shirai, et al., "Photoacid and Photobase Generations: Chemistry and Applications to Polymeric Materials", Prog. Polym. Sci., vol. 21, 1996 (pp. 1-45).
James F. Cameron, et al., "Photogeneration of Organic Bases from o-Nitrobenzyl-Derived Carbamates", J. Am. Chem. Soc. 1991, vol. 113 (pp. 4303-4313).
James F. Cameron, et al., "Base Catalysis in Imaging Materials. 1. Design and Synthesis of Novel Light-Sensitive Urethanes as Photoprecursors of Amines", J. Org. Chem. 1990, vol. 55 (pp. 5919-5922).
Jean M. J. Fréchet, "The Photogeneration of Acid and Base Within Polymer Coatings: Approaches to Polymer Curing and Imaging", Pure & Appl. Chem., vol. 64, No. 9, 1992 (pp. 1239-1248).

(Continued)

*Primary Examiner*—Ann Y Lam
(74) *Attorney, Agent, or Firm*—Julia A. Hodge

(57) ABSTRACT

Methods for fabricating dense arrays of polymeric molecules in a highly multiplexed manner are provided using semiconductor-processing-derived lithographic methods. Advantageously, the methods are adaptable to the synthesis of a variety of polymeric compounds. For example, arrays of branched peptides and polymers joined by peptide bonds may be fabricated in a highly multiplexed manner. Additionally, peptides that adopt helical structures are synthesized on a substrate surface and arrays are created having one or more features containing peptides capable of forming helixes.

16 Claims, 11 Drawing Sheets

OTHER PUBLICATIONS

U.S. Appl. No. 11/395,899, filed Mar. 30, 2006 entitled "Massively Parallel Synthesis of Proteinaceous Biomolecules", Inventor(s): John J. Rajasekaran, et al.

U.S. Appl. No. 11/322,268, filed Dec. 29, 2005 entitled "Massively Parallel Synthesis of Biopoloymeric Arrays", Inventor(s): John J. Rajasekaran, et al.

U.S. Appl. No. 11/585,413, filed Oct. 23, 2006 entitled "Solid-Phase Mediated Synthesis of Molecular Microarrays", Inventor(s): Narayan Sundararajan, et al.

U.S. Appl. No. 11/529,573, filed Sep. 29, 2006 entitled "Method for High Throughput, High Volume Manufacturing of Biomolecule Micro Arrays", Inventor(s): Narayan Sundararajan, et al.

U.S. Appl. No. 11/647,579, filed Dec. 29, 2006 entitled "Fluorogenic Peptide Substrate Arrays for Highly Multiplexed, Real-Time Monitoring of Kinase Activities", Inventor(s): Gunjan Tiwari, et al.

U.S. Appl. No. 11/529,554, filed Sep. 29, 2006 entitled Aptamer biochip for Multiplexed Detection of Biomolecules, Inventor(s): David J. Lui, et al.

U.S. Appl. No. 11/646,600, filed Dec. 28, 2006 entitled "Quality Control Methods for the Manufacture of Polymer Arrays", Inventor(s): Gordon Holt, et al.

U.S. Appl. No. 11/647,580, filed Dec. 29, 2006 entitled "Novel Strategy for Selective Regulation of Background Surface Property in Microarray Fabrication and Method to Eliminate Self Quencing in Micro Arrays", Inventors(s): Edelmira Cabezas et al.

* cited by examiner

A

B

C

D

E

F

Silanation:

Linker coupling:

A

B

C

MOLECULAR MICROARRAYS AND HELICAL PEPTIDES

CROSS-REFERENCE TO RELATED APPLICATIONS

The present application is related to U.S. application Ser. No. 11/395,899, entitled "Massively Parallel Synthesis of Proteinaceous Biomolecules," filed Mar. 30, 2006, now pending, which is a continuation-in-part of U.S. application Ser. No. 11/291,296, filed Nov. 30, 2005, entitled "Massively Parallel Synthesis of Proteinaceous Biomolecules," filed Jun. 6, 2005, now pending; U.S. application Ser No. 11/322,268, entitled "Massively Parallel Synthesis of Biopolymeric Arrays," filed Dec. 29, 2005, now pending; U.S. application Ser. No. 11/529,573, entitled "Method for High Throughput, High Volume Manufacturing of Biomolecule Micro Arrays," filed Sep. 29, 2006, now pending; and U.S. application Ser. No. 11/585,413, entitled "Solid-phase Mediated Synthesis of Molecular Microarrays," filed Oct. 23, 2006, now pending, the disclosures of which are incorporated herein by reference.

BACKGROUND OF THE INVENTION

1. Field of the Invention

Embodiments of the invention relate generally semiconductor lithographic technology, to solid-phase synthesis of microarrays of bio-polymers, peptides and peptide structure, and synthetic organic chemistry.

2. Background Information

Microarrays of oligonucleotides, peptides, proteins, and or oligosaccharides continue to gain importance as powerful tools for research and diagnostic applications in the biomedical sciences. Oligonucleotide microarrays can be used to monitor gene expression and discover genotypes and mutations in a massively parallel manner. Proteinaceous microarrays provide the ability, for example, to characterize the molecular progression of disease, research cellular pathways, and perform high throughput screening in drug discovery applications. Peptide-containing arrays can serve as molecular probes for a variety of biological events, such as for example, the arrays can serve as antigens for antibody-antigen systems, ligands for cell receptor-ligand systems, and substrates for enzyme-protein systems. The ability to collect large volumes of information is an integral part of biomarker discovery and personalization of medical treatments. Further, other applications in bioscience, such as for example, the analysis of the proteomic content of an organism, disease detection, pathogen detection, environmental protection, food safety, and biodefense are capable of benefiting from tools that allow rapid multiplexed interrogation of analyte samples.

As the genomic and proteomic knowledge base expands and the drive toward personalized medicine continues, so does the need for methods to collect, understand, and apply biologically relevant information. Methods, such as analyses using microarrays that allow the use of small volumes of sample for highly multiplexed analyses, are valuable tools. Thus amplifying the value of methods that provide for the controllable automated manufacture of arrays.

One challenge that exists in the design and implementation of peptide microarrays is the tendency of peptides synthesized in vitro and on solid surfaces to adopt random conformations. Three dimensional molecular structure often plays an important role in determining biological function. The random conformation adopted by a peptide synthesized in vitro is not necessarily a biologically active conformation.

DETAILED DESCRIPTION OF THE INVENTION

Figure 1:
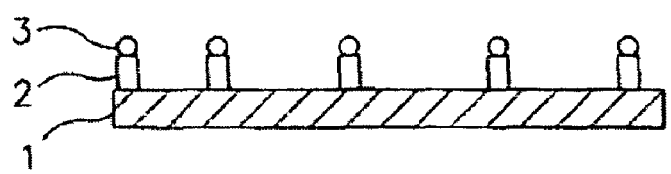
FIGS. 1A through 1F demonstrate a method for the controllable synthesis of polymers on a solid support involving semiconductor lithographic technology.
Figure 1:
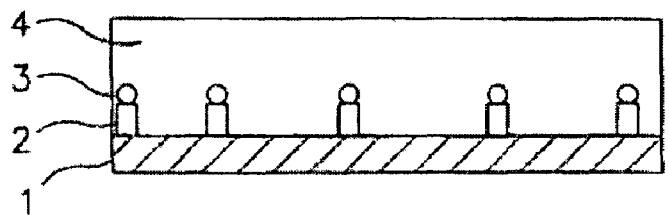
Figure 1:
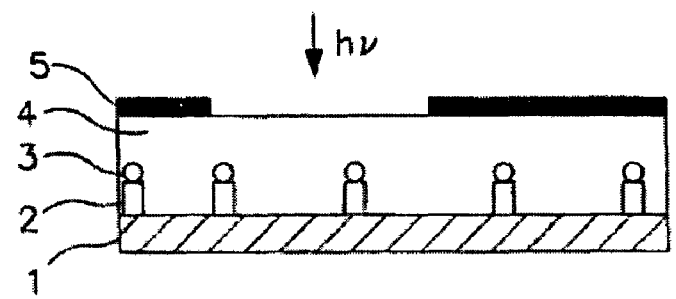
Figure 1:
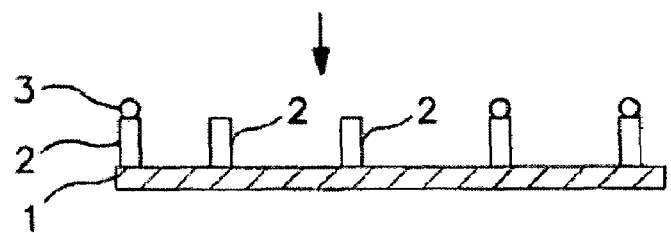
Figure 1:
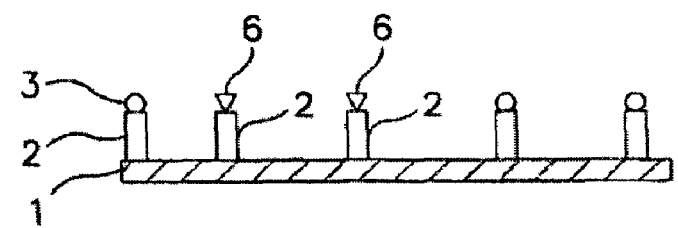
Figure 1:
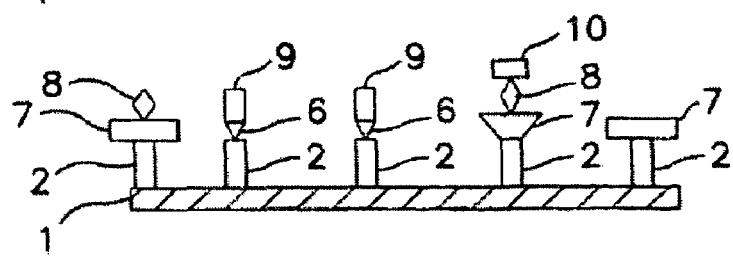

An array is an intentionally-created collection of molecules situated on a solid support in which the identity or source of a group of molecules is known based on its location on the array. The molecules housed on the array and within a feature of an array can be identical to or different from each other. Embodiments of the present invention provide methods for the synthesis of polymers on a solid support. Polymer synthesis according to embodiments of the invention can be accomplished in a manner that provides controlled-density microarrays comprised of peptides, peptoids, peptidemimetics, branched peptides, and or other small bio-molecules. Embodiments of the present invention provide arrays of biopolymers of known sequence and controllable molecular density. Additionally, the methods described in embodiments of the invention are highly scalable for array manufacture on a wafer or chip as are used in to fabricated devices in the semiconductor industry.

The features, regions, or sectors of an array in which the bio-polymers are located may have any convenient shape, for example, the features of the array may be circular, square, rectangular, elliptical, or wedge-shaped. In some embodiments, the region in which each distinct biomolecule is synthesized within a feature is smaller than about 1 $mm^2$, or less than 0.5 $mm^2$. In further embodiments the features have an area less than about 10,000 $\mu m^2$ or less than 2.5 $\mu m^2$. Additionally, multiple copies of a polymer will typically be located within any feature. The number of copies of a polymer can be in the thousands to the millions within a feature. In general, an array can have any number of features, and the number of features contained in an array may be selected to address such considerations as, for example, experimental objectives, information-gathering objectives, and cost effectiveness. An array could be, for example, a 20×20 matrix having 400 regions, 64×32 matrix having 2,048 regions, or a 640×320 array having 204,800 regions. Advantageously, the present invention is not limited to a particular size or configuration for the array.

A method for synthesizing polymers within one or more selected region(s) of a solid support is shown in FIGS. 1A-F.

In general, the method includes attachment of a first amino acid, linker (or spacer) molecule, or other building block 2 to the surface of a substrate 1. Additionally, mixtures of different building blocks 2 may also be used. For example, in FIG. 1A a first building block 2 can be an amino acid that is attached to a substrate 1 that is comprised of amino-functionalized glass, through the formation of a peptide bond between the carboxylate of the amino acid and the amine group of the glass. The terminal bond-forming site of the building block 2 is protected with a protecting group 3. For example, the α-amino group of an amino acid can be protected with an N-protecting group 3 to prevent unwanted reactivity. If necessary, a side chain of the building block (for example, an R group of an amino acid) may also have a protecting group. Suitable protecting groups include, for example, t-butoxycarbonyl (t-BOC), and fluorenylmethoxycarbonyl (FMOC), and 2-(4-biphenylyl)-2-oxycarbonyl. Advantageously, embodiments of the present invention are not limited to the type of acid- or base-removable protective group or building block selected.

Referring now to FIG. 1B, once the first polymer building block has been attached to a substrate, a layer of photoresist 4 is deposited over the substrate 1 surface. In embodiments of the invention, the photoresist layer can be created from a solution comprising a polymer, a photosensitizer, and a photo-active compound or molecule in a solvent. The photoresist can be applied using any method known in the art of semiconductor manufacturing for the coating of a wafer with a photoresist layer, such as for example, the spin-coating method. The photoresist-coated substrate is then baked to remove excess solvent from the photoresist and for film uniformity.

In FIG. 1C, a photomask 5 is placed over photoresist layer 4. The photomask use may be practiced according to standard techniques and materials used in the semiconductor fabrication industry. For example, the photomask 5 may be a transparent pane, such as a quartz pane, having an emulsion or metal film on a surface creating the mask pattern. Suitable metals include chromium. The pattern of the mask is chosen so that regions on the surface of the substrate can be selectively activated for polymer synthesis. Radiation, for example, ultra violet radiation (UV) or deep ultraviolet radiation (DUV), may then be directed through the photomask 5 onto the photoresist layer. The photoresist 4 is exposed in those regions of the mask that are transparent to the impinging radiation. In general, the device used for creating a pattern in the photoresist can be a physical mask or any other source capable of projecting a pattern image, for example a micromirror.

The exposure of the photoresist 4 to radiation generates cleaving reagents (species that catalyze the removal of a protective group, for example) in the exposed portion of the photoresist layer 4. The generation of cleaving reagents in the photoresist may be the result of a number of processes. For example, the cleaving reagent may result from the direct radiation-induced decomposition of or chemical transformation of a photoactive cleavage reagent precursor compound. Alternatively or in addition, generation of the cleaving reagent may occur through the absorption of light by a photosensitizer followed by reaction of the photosensitizer with the cleavage reagent precursor, energy transfer from the photosensitizer to the cleavage reagent precursor, or a combination of two or more different mechanisms.

As a result of the radiation-induced generation of the cleaving reagent, the protecting groups 3 are cleaved from the molecules 2 under the exposed area(s) of the photoresist. The molecules 2 located under the unexposed masked regions remain unreacted. The cleaving process leading to the removal of the protecting groups 3 may, for example, be acid-catalyzed cleavage or base-catalyzed cleavage. The chemistry of the process will depend on the type of protecting groups 3 and on the type of cleaving reagents that are generated in the photoresist upon radiation exposure. For example, if the protecting group 3 is t-BOC, acid cleavage can be used. Acids may be generated in the photoresist, for example, through the exposure of sulfonium or halonium salts to radiation. If the protecting group is FMOC, for example, then base cleavage can be used. Cleavage can be accomplished through the reaction of a photogenerated amine or diamine through a decarboxylation process. The rate of protecting group removal can be accelerated by heating the substrate after the exposure to radiation (post exposure bake). The post exposure bake (PEB) serves multiple purposes in photoresist processing. First, the elevated temperature of the bake drives diffusion of the photoproducts. A small amount of diffusion can be useful in minimizing the effects of standing waves, periodic variations in exposure dose throughout the depth of the film that result from interference of incident and reflected radiation. The other main purpose of the PEB is to drive the acid-catalyzed reaction. Chemical amplification is important because it allows a single photoproduct to cause many solubility-switching reactions, thus increasing the sensitivity of these photoresist systems.

Subsequent to the exposure of the masked substrate to radiation, the photoresist is removed. The photoresist layer 4 may be removed using acetone or another similar suitable solvent. The resulting surface-modified substrate is shown schematically in FIG. 1D. In this structure, there are three regions shown: two regions that have protected molecules and a region having deprotected molecules. The deprotected molecules are available for further reaction, such as for example, a peptide-bond forming coupling reaction whereas the molecules that retain their protective groups are not available for further reaction. Solid phase peptide synthesis can be carried out using standard techniques, see for example, Bodansky, M., Bodansky, A., *The Practice of Peptide Synthesis* ($2^{nd}$ edition), Springer Verlag, Berlin (1995); Stewart, J. M., Young, J. D., *Solid Phase Peptide Synthesis* ($2^{nd}$ edition), Pierce Chemical Company, Rockford Ill., (1984); *Solid-Phase Peptide Synthesis: Methods in Enzymology*, vol. 298, Academic Press (1997); and for synthesis of peptides and peptidomimetics: *Methods in Organic Chemistry*, vol. E22, Houben Weyl (2004). FIG. 1E shows a structure resulting from the reaction of the deprotected surface-attached molecules. In FIG. 1E, a building block 6 has been added to molecule 2. Building block 6 may be the same or different from molecule 2. The building block 6 is protected with a protecting group to prevent unwanted reactions.

The processes illustrated in FIGS. 1A-E may be repeated to form polymers on the substrate surface. Through the selection of different mask configurations, different polymers comprising building blocks 2 and 6-10 may be formed in regions upon the surface, as shown schematically in FIG. 1F. In the case where the building blocks are amino acids, peptides having the same or different known sequences are formed in known regions on the surface of the substrate. In general, polymers containing from about 2 to about 50 mers (polymeric units) can be created. In embodiments of the invention peptides having a length of about 6 to about 20 amino acids are created.

Any unreacted deprotected chemical functional groups may be capped at any point during a synthesis reaction to avoid or to prevent further bonding at such molecule. In general, capping reagents can be a reagent that prevents further reactivity at the site of polymer chain formation such as, for example, an acid anhydride without further reactive functionalities. Capping groups cap deprotected functional groups by, for example, binding with the unreacted amino functions to form amides. Capping agents suitable for use in an embodiment of the invention include: acetic anhydride, n-acetylimidizole, isopropenyl formate, fluorescamine, 3-nitrophthalic anhydride and 3-sulfoproponic anhydride.

In general, peptides are polymers of amino acids, amino acid mimics or derivatives, and/or unnatural amino acids. The amino acids can be any amino acids, including $\alpha$, $\beta$, or $\omega$-amino acids and modified amino acids. When the amino acids are $\alpha$-amino acids, either the L-optical isomer or the D-optical isomer may be used. In general, an amino acid contains an amine group, a carboxylic group, and an R group. The R group can be a group found on a natural amino acid or a group that is similar in size to a natural amino acid R group. Additionally, unnatural amino acids, for example, $\beta$-alanine, phenylglycine, homoarginine, aminobutyric acid, aminohexanoic acid, aminoisobutyric acid, butylglycine, citrulline, cyclohexylalanine, diaminopropionic acid, hydroxyproline, norleucine, norvaline, ornithine, penicillamine, pyroglutamic acid, sarcosine, and thienylalanine are also contemplated by the embodiments of the invention. These and other natural and unnatural amino acids are available from, for example, EMD Biosciences, Inc., San Diego, Calif.

A peptide is a polymer in which the monomers are amino acids, a group of molecules which includes natural or unnatural amino acids, amino acid mimetics, and amino acid derivatives, which are generally joined together through amide (peptide) bonds. A peptide can alternatively be referred to as a polypeptide. Peptides contain two or more amino acid monomers, and often more than 50 amino acid monomers (building blocks).

A protein is a long polymer of amino acids linked via peptide bonds and which may be composed of one or more polypeptide chains. More specifically, the term protein refers to a molecule comprised of one or more polymers of amino acids. Proteins are essential for the structure, function, and regulation of the body's cells, tissues, and organs, and each protein has unique functions. Examples of proteins include some hormones, enzymes, and antibodies.

A protecting group is a group which is bound to a molecule and designed to block a reactive site in a molecule, but may be removed upon exposure to an activator or a deprotecting reagent. Deprotecting reagents include, for example, acids and bases. Protecting groups can be bound to a monomer, a polymer, a linker molecule or a monomer, or polymer, or a linker molecule attached to a solid support to protect a reactive functionality on the monomer, polymer, or linker molecule. Protective groups that may be used in accordance with an embodiment of the invention include all acid and base labile protecting groups. For example, peptide amine groups are preferably protected by t-butoxycarbonyl (t-BOC or BOC) or benzyloxycarbonyl (CBZ), both of which are acid labile, or by 9-fluorenylmethoxycarbonyl (FMOC), which is base labile.

Additional protecting groups that may be used in accordance with embodiments of the invention include acid labile groups for protecting amino moieties: tert-amyloxycarbonyl, adamantyloxycarbonyl, 1-methylcyclobutyloxycarbonyl, 2-(p-biphenyl)propyl(2)oxycarbonyl, 2-(p-phenylazophenyl)propyl(2)oxycarbonyl, .alpha.,.alpha.-dimethyl-3,5-dimethyloxybenzyloxy-carbonyl, 2-phenylpropyl(2)oxycarbonyl, 4-methyloxybenzyloxycarbonyl, furfuryloxycarbonyl, triphenylmethyl(trityl), p-toluenesulfenylaminocarbonyl, dimethylphosphinothioyl, diphenylphosphinothioyl, 2-benzoyl-1-methylvinyl, o-nitrophenylsulfenyl, and 1-naphthylidene; as base labile groups for protecting amino moieties: 9-fluorenylmethyloxycarbonyl, methylsulfonylethyloxycarbonyl, and 5-benzisoazolylmethyleneoxycarbonyl; as groups for protecting amino moieties that are labile when reduced: dithiasuccinoyl, p-toluene sulfonyl, and piperidino-oxycarbonyl; as groups for protecting amino moieties that are labile when oxidized: (ethylthio)carbonyl; as groups for protecting amino moieties that are labile to miscellaneous reagents, the appropriate agent is listed in parenthesis after the group: phthaloyl (hydrazine), trifluoroacetyl (piperidine), and chloroacetyl (2-aminothiophenol); acid labile groups for protecting carboxylic acids: tert-butyl ester; acid labile groups for protecting hydroxyl groups: dimethyltrityl. See also, Greene, T. W., *Protective Groups in Organic Synthesis*, Wiley-Interscience, NY, (1981).

A linker molecule typically is a molecule inserted into the growing polymer that does not necessarily convey functionality to the resulting peptide, such as molecular recognition functionality, but instead elongates the distance between the substrate surface and the peptide functionality to enhance the exposure of the peptide functionality on the surface of the substrate. Preferably a linker should be about 4 to about 40 atoms long to provide exposure. The linker molecules may be, for example, aryl acetylene, ethylene glycol oligomers containing 2-10 monomer units (PEGs), diamines, diacids, amino acids, among others, and combinations thereof. Examples of diamines include ethylene diamine and diamino propane. Alternatively, the linkers may be the same molecule type as that being synthesized (i.e., nascent polymers), such as polypeptides and polymers of amino acid derivatives such as for example, amino hexanoic acids.

Solid support, support, and substrate refer to a material or group of materials having a rigid or semi-rigid surface or surfaces. In some aspects, at least one surface of the solid support will be substantially flat, although in some aspects it may be desirable to physically separate synthesis regions for different molecules with, for example, wells, raised regions, pins, etched trenches, or the like. In certain embodiments, the solid support may be porous.

Substrate materials useful in embodiments of the present invention include, for example, silicon, bio-compatible polymers such as, for example poly(methyl methacrylate) (PMMA) and polydimethylsiloxane (PDMS), glass, $SiO_2$ (such as, for example, a thermal oxide silicon wafer such as that used by the semiconductor industry), quartz, silicon nitride, functionalized glass, gold, platinum, and aluminum. Functionalized surfaces include for example, amino-functionalized glass, carboxy functionalized glass, and hydroxy functionalized glass. Additionally, a substrate may optionally be coated with one or more layers to provide a surface for molecular attachment or functionalization, increased or decreased reactivity, binding detection, or other specialized application. Substrate materials and or layer(s) may be porous or non-porous. For example, a substrate may be comprised of porous silicon. Additionally, the substrate may be a silicon wafer or chip such as those used in the semiconductor device fabrication industry. In the case of a wafer or chip, a plurality of arrays may be synthesized on the wafer.

Photoresist formulations useful in the present invention include a polymer, a solvent, and a radiation-activated cleaving reagent. Useful polymers include, for example, poly(methyl methacrylate) (PMMA), poly-(methyl isopropenyl ketone) (PMPIK), poly-(butene-1-sulfone) (PBS), poly-(trifluoroethyl chloroacrylate) (TFECA), copolymer-($\alpha$-cyano ethyl acrylate-$\alpha$-amido ethyl acrylate) (COP), and poly-(2-methyl pentene-1-sulfone). Useful solvents include, for example, propylene glycol methyl ether acetate (PGMEA), ethyl lactate, and ethoxyethyl acetate. The solvent used in fabricating the photoresist may be selected depending on the particular polymer, photosensitizer, and photo-active compound that are selected. For example, when the polymer used in the photoresist is PMMA, the photosensitizer is isopropyl-thioxanthenone, and the photoactive compound is diphenyliodonium chloride, PGMEA or ethyl lactate may be used as the solvent.

In exemplary photoresist formulations, the mass concentration of the polymer may between about 5% and about 50%, the mass concentration of a photosensitizer may be up to about 20%, the mass concentration of the photo-active compound may be between about 1% and 10%, the balance comprising a suitable solvent. After the photoresist is deposited on the substrate, the substrate typically is heated to form the photoresist layer. Any method known in the art of semiconductor fabrication may be used to for depositing the photoresist solution. For example, the spin coating method may be used in which the substrate is spun typically at speeds between about 1,000 and about 5,000 revolutions per minute for about 30 to about 60 seconds. The resulting wet photoresist layer has a thickness ranging between about 0.1 μm to about 2.5 μm.

Catalysts for protective group removal (also referred to as cleaving reagents) useful in the present invention include acids and bases. For example, acids can be generated photochemically from sulfonium salts, halonium salts, and polonium salts. Sulfonium ions are positive ions, $R_3S^+$, where R is, for example, a hydrogen or alkyl group, such as methyl, phenyl, or other aryl group. For example, trimethyl sulfonium iodide and triaryl sulfonium hexafluroantimonatate (TASSbF$_6$) are useful sulfonium ion containing compounds. In general, halonium ions are bivalent halogens, $R_2X^+$, where R is a hydrogen or an alkyl group, such as methyl, phenyl, or other aryl group, and X is a halogen atom. The halonium ion may be linear or cyclic. Polonium salt refers to a halonium salt where the halogen is iodine, the compound $R_2I^+Y^-$, where Y is an anion, for example, a nitrate, chloride, or bromide. For example, diphenyliodonium chloride and diphenyliodonium nitrate are useful halonium salt containing compounds. See also, Frechet, J. M. J., Ito, H., Willson, C. G., *Proc. Microcircuit Eng.*, 260, (1982); Shirai, M., Tsunooka, M., *Prog. Polym. Sci.*, 21:1, (1996); Frechet, J. M. J., Eichler, E, Ito, H., Willson, C. G., *Polymer,* 24:995, (1983); and Frechet, J. M. J., Ito, H., Willson, C. G., Tessier, T. G., Houlihan, F. M. J., *J. of Electrochem. Soc.,* 133:181 (1986).

Photogenerated bases include amines and diamines having photolabile protecting groups. See for example, Shirai, M., Tsunooka, M., *Prog. Polym. Sci.,* 21:1, (1996); Comeron, J. F., Frechet, J. M. J., *J. Org. Chem.,* 55:5919, (1990); Comeron, J. F., Frechet, J. M. J., *J. Am. Chem. Soc.,* 113:4303, (1991); and Arimitsu, K. and Ichimura, K., *J. Mat. Chem,.* 14:336, (2004).

Optionally, the photoresists useful in the present invention may also include a photosensistizer. In general, a photosensitizer absorbs light and interacts with the cleavage reagent precursor, through one or more mechanisms, including, reaction with the cleavage reagent precursor and energy transfer from the photosensitizer to the cleavage reagent precursor. Useful photosensitizers include, for example, benzophenone and other similar diphenyl ketones, thioxanthenone, isopropyl-thioxanthenone, anthraquinone, fluorenone, acetophenone, and perylene.

Figure 2:
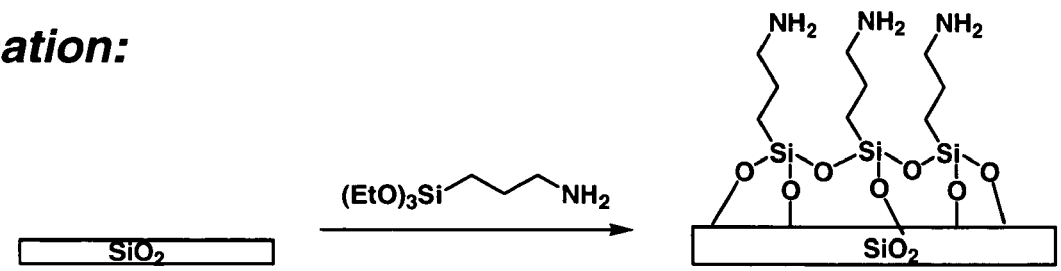
FIG. 2 shows a method for derivatizing a $SiO_2$ surface and attaching a linker molecule to the derivatized surface.
Figure 2:
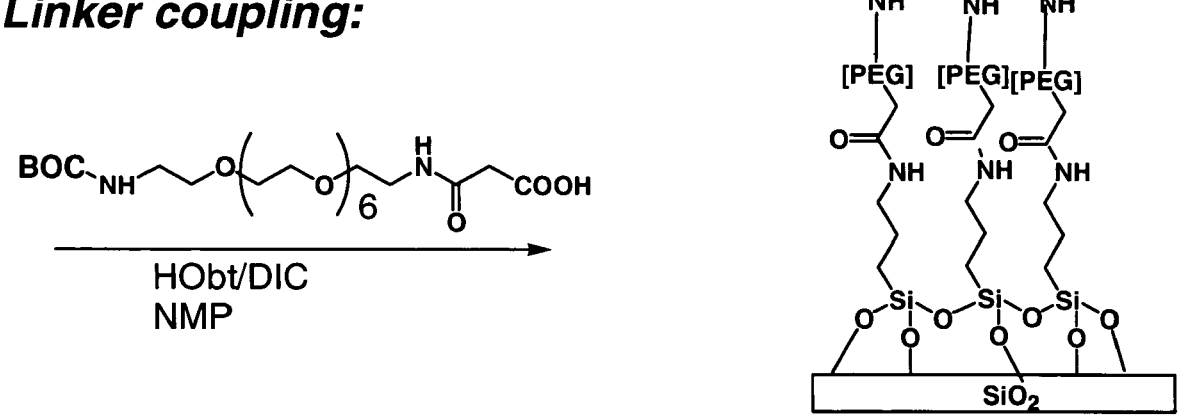

FIG. 2 provides a method for derivatization of a SiO$_2$ surface and linking of polymeric molecules to the surface. In FIG. 2 the SiO$_2$ surface is silanated by reacting it with aminopropyltriethoxy silane (APTES). The resulting surface presents an amine functional group for further reaction, such as peptide bond formation. Modulation of the density of polymers on the surface can be attained by silanation. For example, density can be modulated by mixing a functionalizable silane for example, APTES, with a non-functional silane (a silane with no non silyl functional group), for example, propyltrialkoxy silane. The derivatized surface can then be reacted with a linker. In this example, the linker is a polyethylene glycol molecule having an amine group protected with BOC at one terminus and a peptide-bond forming group (a carboxyl group) at the second terminus. This coupling reaction can be accomplished in a solution of carboxyl group activators: 1-hydroxybenzotriazole (HOBt) and diisopropylcarbodiimide (DIC) in N-methyl pyrrolidone (NMP). The linker molecule serves to separate polymer (peptide) that is subsequently synthesized from surface of the substrate.

Figure 3:
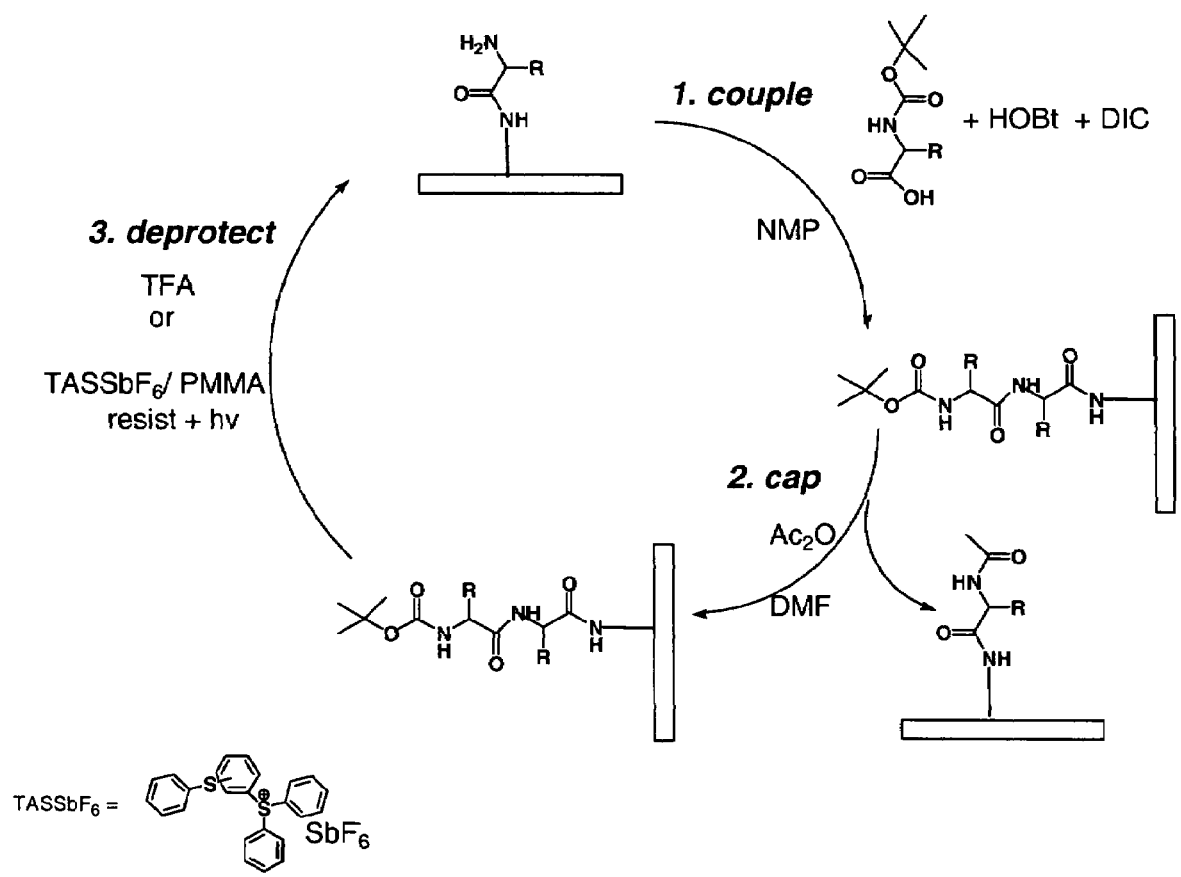
FIG. 3 demonstrates general methods for solid phase peptide synthesis.

FIG. 3 shows a general scheme for solid-phase peptide synthesis. A substrate surface is provided having a first amino acid attached to the surface. A second amino acid having an amino protecting group is coupled to the first amino acid. In this example, the second amino acid is N-protected with a BOC protecting group. The coupling reaction is performed in a solution of 1-hydroxybenzotriazole (HOBt) and diisopropylcarbodiimide (DIC) in N-methyl pyrrolidone (NMP). Unreacted amine groups are capped using an acetic anhydride (Ac$_2$O) solution in dimethylformamide (DMF). The substrate surface is then coated with a photoresist. In this example, the photoresist is comprised of PMMA polymer, TASSbF$_6$ (photoactivated acid generator), and PGMEA (as a solvent). In FIG. 3, TFA represents trifluoroacetic acid, the acidic cleaving reagent typically used for bulk solid-phase peptide synthesis. Experiments demonstrated that yields for a peptide synthesis process according to the current invention were similar to yields for bulk solid-phase synthesis procedures using TFA as a protecting group removal catalyst. Upon exposure to radiation, in this case UV radiation, an acid is produced in the photoresist and the N-protecting group is removed from the attached peptide in the region of UV exposure. By repeating the process shown in FIG. 3, peptides of desired sequence and length in selected regions upon the substrate surface can be produced.

Figure 4:
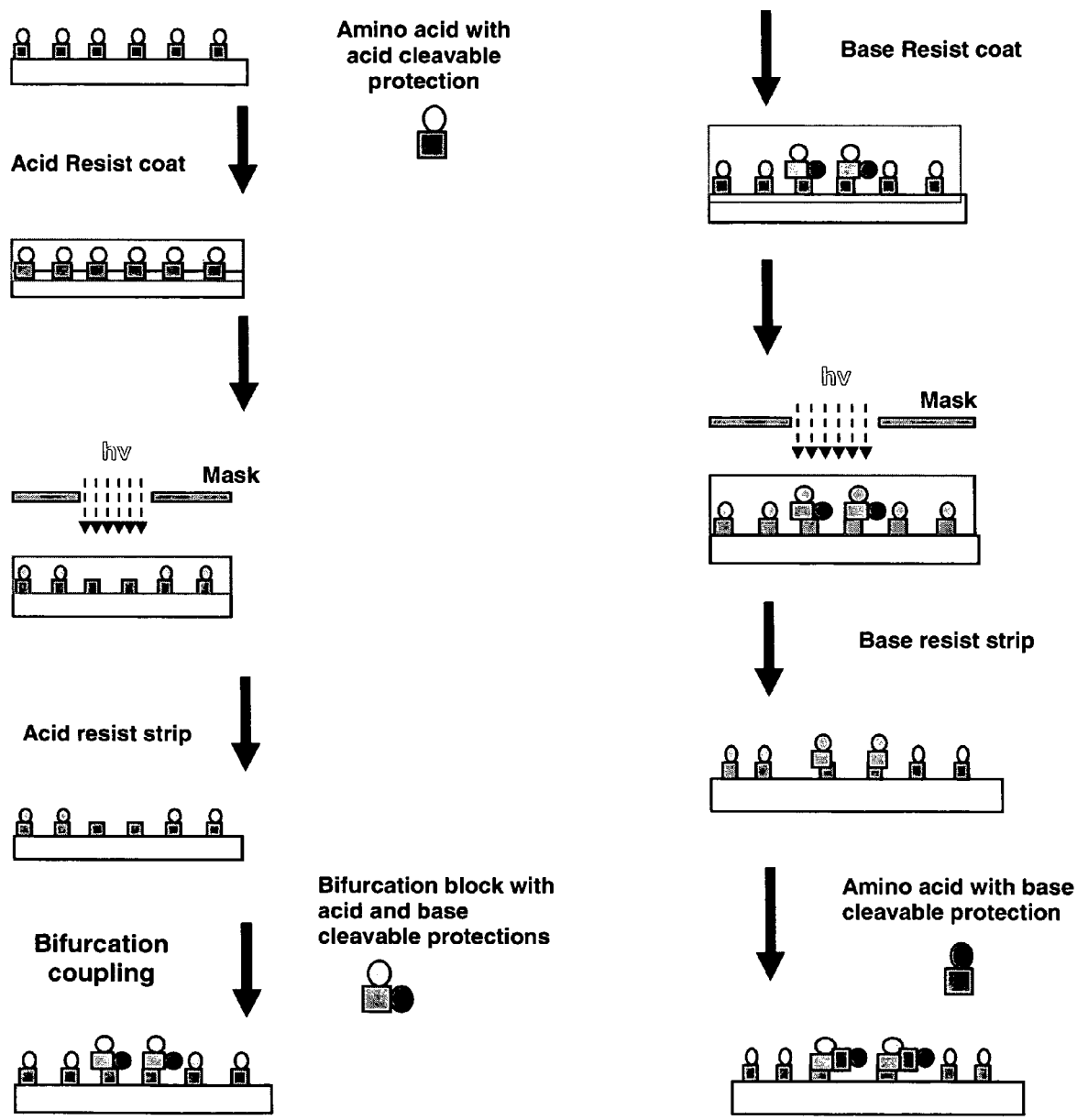
FIG. 4 demonstrates a general method for the synthesis of branched proteinaceous molecules on a solid surface that can be used to create arrays of molecules.

FIG. 4 diagrams a method for using semiconductor photoresist acid and base cleavage mechanisms and orthogonal protection chemistries to create a branch point in a growing solid-phase polymer chain. In FIG. 4, a region of a substrate surface presents an attached amino acid building block containing an acid-cleavable protecting group that prevents the formation of a peptide bond. As described herein, the amino acid building block may be attached to the surface through a linker molecule that spaces the amino acid from the surface and or that functions as a peptide or peptidemimetic. The substrate surface is coated with an acid-generating photoresist and at least one region of the substrate surface is exposed to radiation to induce the formation of the photo-generated acid in the photoresist. A mask is used to selectively block the radiation from areas of the substrate surface and thereby cause deprotection of only molecules located in selected regions of the substrate surface. Preferably, the substrate surface is subjected to a post-exposure bake. The photoresist is then stripped from the substrate surface leaving a section(s) of the substrate having deprotected sites available for the formation of peptide bonds. A bifurcation group is coupled to the deprotected growing chain. Optionally, the bifurcation group contains both acid and base cleavable protecting groups, only acid cleavable protecting groups, or only base cleavable protecting groups. The branch points of the bifurcation group can be selectively deprotected by selecting either an acid or a base-generating photoresist. In the scheme shown in FIG. 4, the bifurcation group has both acid and base cleavable protecting groups and a base-generating photoresist is selected and the base-cleavable protecting group is removed from the bifurcation group upon irradiation. The surface is baked and the resist removed. An amino acid having a base-removable protecting group is coupled to the bifurcation group at the point in which the base-removable group was removed. Alternatively or subsequently, the acid labile protecting group may be removed in a similar manner using a photoresist containing a photogenerated acid as described herein. An amino acid having an acid-removable protecting group is then coupled to the bifurcation group. Repetitions of these acid or base deprotection-coupling events allow a branched polymer having a desired sequence to be synthesized. The polymers formed from the branch-point may be the same or different lengths. Additionally, optionally polymers having one or more branch points may be created. An array may be created having both branched and unbranched polymers in regions upon its surface.

Figure 5:
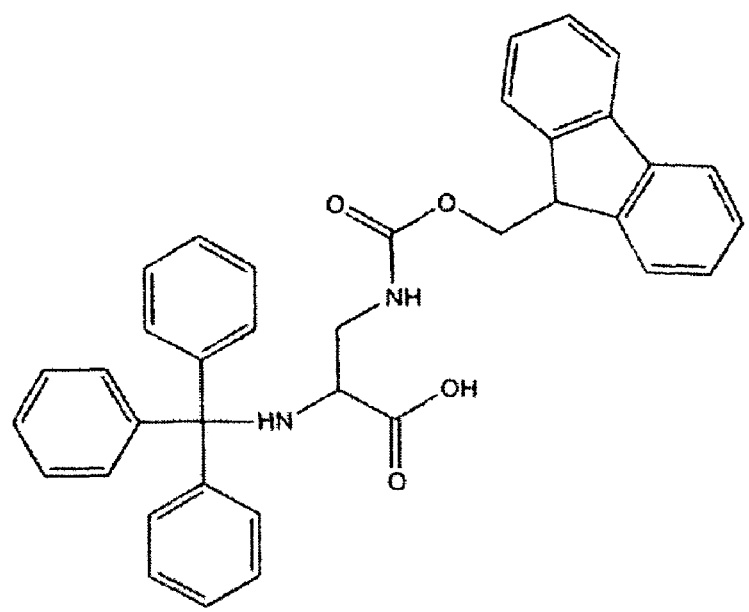
FIGS. 5A-C provide exemplary bifurcation molecules.
Figure 5:
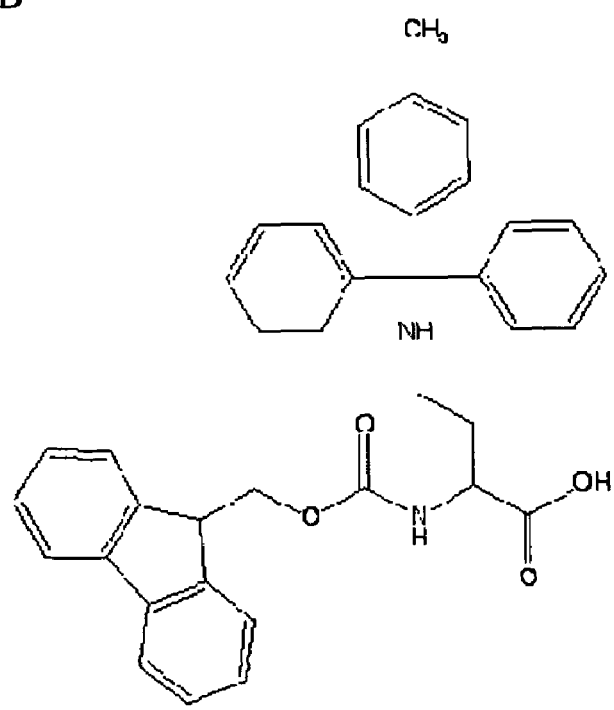
Figure 5:
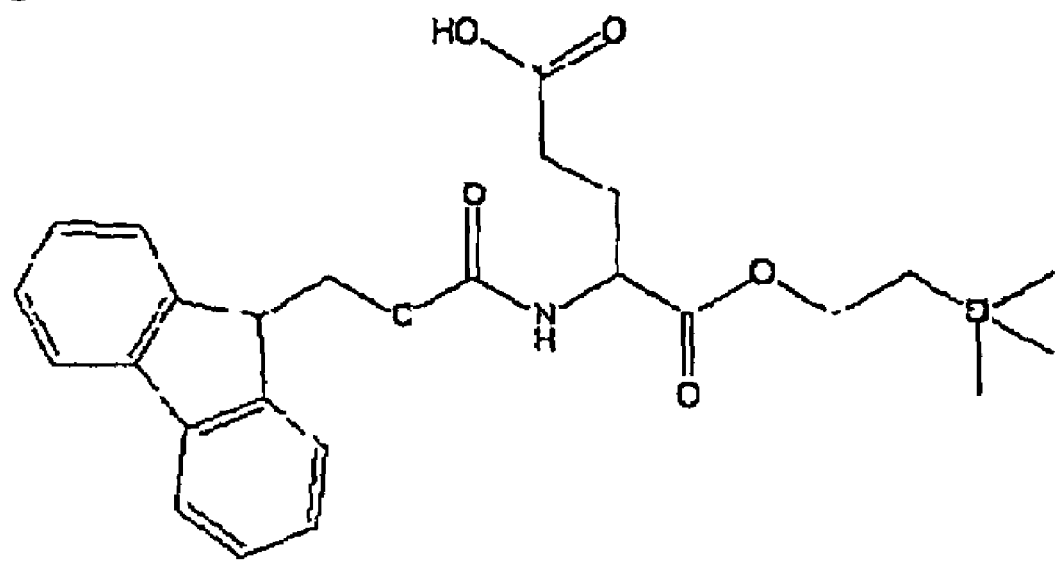

In general, a bifurcation molecule is a molecule that when it is attached to a growing polymer provides more than one location for further polymer growth or extension. In other words, a bifurcation molecule is a polymeric building block that creates a branch point in a polymer. FIGS. 5A-C provide several exemplary bifurcation molecules: FIG. 5A shows Trt-Dpr(Fmoc)-OH (Dpr is diaminopropionic acid); FIG. 5B shows Fmoc-Dab(Mtt)-OH ("Dab" is diaminobutanoic acid, "Mtt" is 4-methyltrityl, an acid-removable protecting group); FIG. 5C shows Fmoc-Glu-OTMSEt ("OTMSEt" is trimethylsilylethanol). Additional examples of useful bifurcation molecules include Fmoc-Dpr(Boc)-OH, Fmoc-Dab(Boc)-OH, or any of the previous amino acids having the same protecting group at the amino and the side chain functionalities (to allow growth of two peptide chains having the same sequence), such as for example, Fmoc-Dpr(Fmoc)-OH or Trt-Dpr(Trt)-OH. Many bifurcation molecules are available from EMD Biosciences Nova Biochem, La Jolla, Calif.; Bachem, Torrance, Calif.; and Chem-Impex International.

Figure 6:
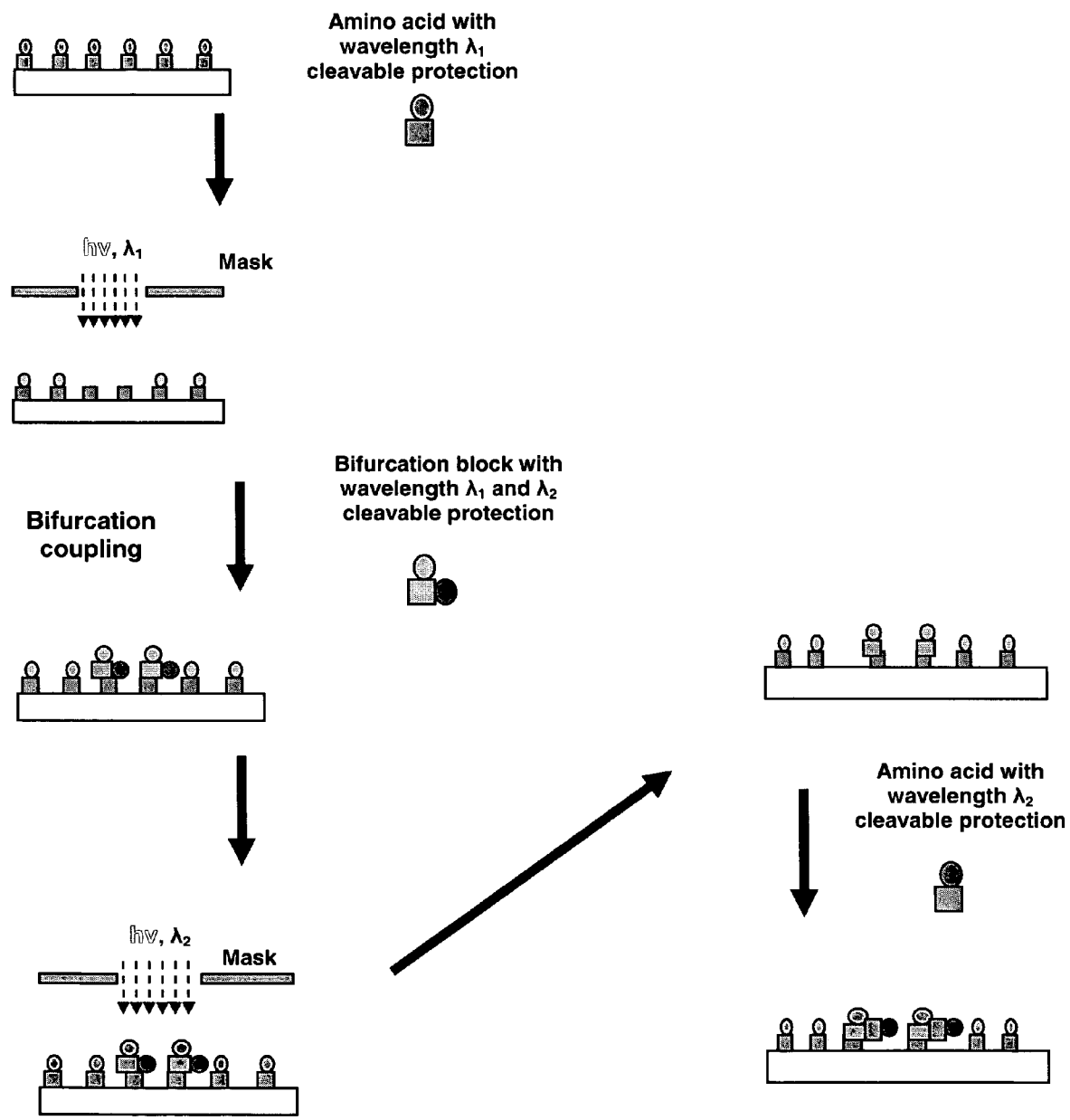
FIG. 6 outlines an additional method for the synthesis of branched proteinaceous molecules on a solid surface that can be used to create arrays of biomolecules.

FIG. 6 diagrams a further method by which branch points can be created in a polymer using orthogonal protection strategies and solid-phase bio-polymer synthesis. In FIG. 6, direct photo-cleavage lithography is applied to the synthesis of a branched peptide array. In this example, a region of a substrate surface presents an attached amino acid building block containing a photo-cleavable protecting group that prevents the formation of a peptide bond. As described herein, the amino acid building block may be attached to the surface through a linker molecule that spaces the amino acid from the surface and or that functions as a peptide or peptidemimetic. The photo-cleavable protecting group is removable at a first wavelength, $\lambda_1$. Exposing the substrate through a mask to radiation at a first wavelength, $\lambda_1$, removes the protecting group in selected regions. A bifurcation group having photo-cleavable protecting groups that are removable at two different wavelengths, $\lambda_1$ and $\lambda_2$, is coupled to the photo-deprotected amino acid building blocks. In the example of FIG. 6, a selected area(s) of the substrate surface are exposed to light of wavelength $\lambda_2$ and the $\lambda_2$ photo-removable protecting group is removed. An amino acid building block having a $\lambda_2$ photo-removable protecting group is coupled to the deprotected site of the bifurcation group. Alternately or subsequently, a selected area(s) of the substrate surface are exposed to light of wavelength $\lambda_1$ and the $\lambda_1$ photo-removable protecting group is removed. An amino acid building block having a $\lambda_1$ photo-removable protecting group is coupled to the deprotected site of the bifurcation group. Repetitions of these photo-deprotection-coupling events allow a branched polymer having a desired sequence to be synthesized. The polymers formed from the branch-point may be the same or different lengths. Additionally, optionally polymers having one or more branch points may be created. An array may be created having both branched and unbranched polymers in regions upon its surface.

Some examples of wavelength controlled orthogonal protecting groups are described in "Wavelength-Controlled Orthogonal Photolysis of Protecting Groups," Blanc, A. and Bochte, C., *J. Org. Chem.*, 67:5567 (2002). Additional examples of photo-cleavable protecting groups can be found in: *Photogenerated Reagents in Biochemistry and Molecular Biology*, Bayley, H., Laboratory Techniques in Biochemistry and Molecular Biology, 12, Elsevier (2002); and Clark, M. A. and Romoff, T. T., Synthesis of peptides and peptidomimetics, *Methods of Organic Chemistry*, E22a:276 (2004). The most common photocleavable groups are 2-nitrobenzyl-derived carbamates, esters, and ethers. Examples include Z(2-NO2), Nvoc, Ndmoc, Dnboc, Menpoc, Ddz. Other examples include tosyl, phenacyl-based esters, and the 5-bromo-7-nitro-indolinyl group. Many amino acids with photocleavable protecting groups are available from Chem-Impex International, Wood Dale, Ill.

Figure 7:
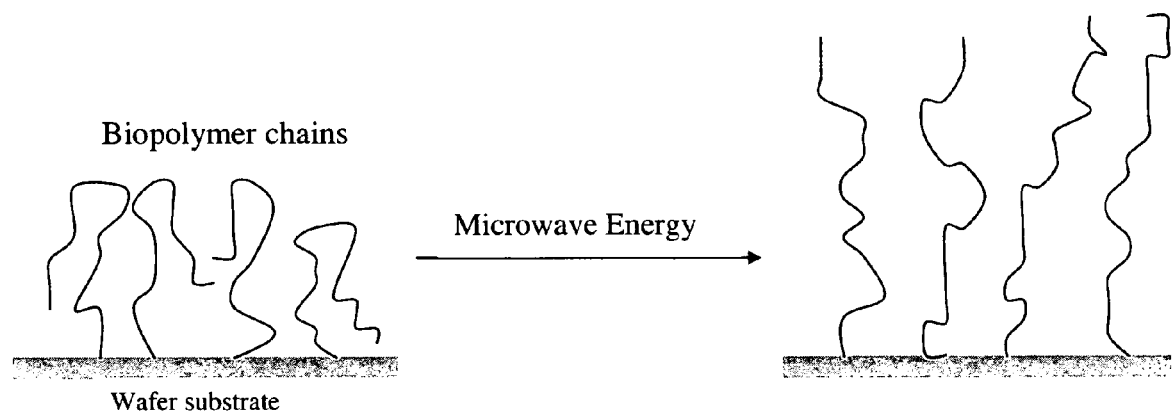
FIG. 7 diagrams the effect of the application of microwave energy to a substrate surface having attached polymers.

In further embodiments of the present invention, methods are provided to synthesize biopolymers on an array wherein the synthesis is assisted by microwave radiation. Organic synthesis reactions that are assisted by microwave radiation generally demonstrate faster rates and improved fidelity. Synthesis of biopolymers, particularly parallel synthesis methodologies can encounter difficulties, depending on the species being synthesized, from intermolecular aggregation, hydrogen bonded secondary structures (such as, for example, beta-sheet formation in peptides), steric hindrance from bulky side chain protecting groups, and hence premature termination of the sequence. Referring now to FIG. 7, a schematic is presented showing the microwave heating of polymers on a substrate surface. In this example, the heating of the polymers causes them to unwind. In the microwave-assisted solid phase synthesis of polymer chains, microwave energy directly activates any molecule with a dipole moment and allows for local heating at a molecular level. Thus, intermolecular and intramolecular aggregation, secondary structure formation, and steric hindrance can be overcome with microwave energy. Additionally, by using microwave energy in conjunction with parallel synthesis methods, reaction times for deprotection and coupling reactions can be reduced and fidelity of lithographic techniques can be enhanced.

Figure 8:
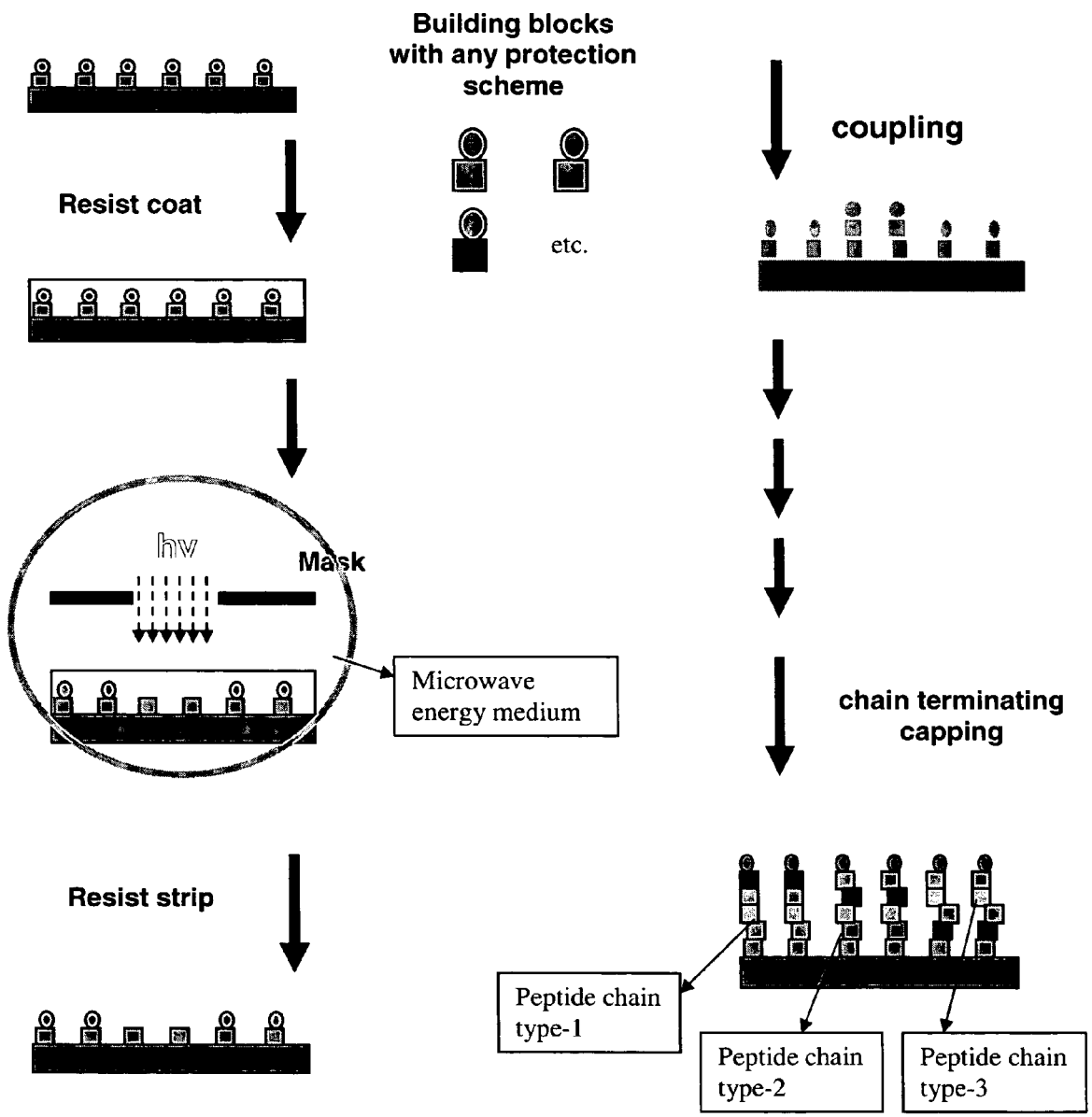
FIG. 8 diagrams the use of microwave energy in the photoresist method for peptide parallel synthesis.

FIG. 8 shows the use of microwave energy to assist the synthesis of biopolymers on a solid support. In general, microwave energy can be used to facilitate the synthesis of branched and unbranched biopolymers, such as for example, peptides, peptidemimetics, and polynucleotides, by photoresist methods and methods employing photo-removable protecting groups, as described herein and as known in the art. The term polynucleotide includes oligonucleotides, peptide nucleic acids (PNAs), and cDNA. In FIG. 8, a substrate surface presents attached biopolymer building blocks having a protecting group that prevents polymer formation. The substrate is coated with a photoresist. Selected areas of the substrate are exposed to radiation through a mask to remove the protecting group in the presence of microwave energy. The photoresist is removed and a second building block having a protecting group is coupled to the first deprotected building block. These steps are repeated for form desired polymers, in this case the polymers are peptides, at desired locations on the substrate surface. Synthesizers generally supply microwave power of about 25 to 50 W and a temperature range of 20 to 70° C. Additionally, microwave energy can be employed in the manufacture of arrays on silicon chips. In this case a microwave stepper and a microwave synthesizer can be used to manufacture a plurality of arrays in a similar manner as it is employed in the semiconductor fabrication industry.

Protein activity is directly associated with its three-dimensional structure. The active site of a protein is usually comprised of a few amino acid residues that can be close to each other (continuous site) or far apart (discontinuous sites) in the primary amino acid sequence of the protein. The activity of a peptide sequence (short amino acid sequence) containing the sequence of a continuous active site is almost never similar to the activity of the folded protein. The lack of activity found for peptides is most often because peptides do not adopt specific conformations (three-dimensional structures). Short peptides sequences synthesized in vitro adopt random conformations (mixtures of many conformations), consequently their activity can be poor even if, for example, the peptide corresponds to the amino acid sequence found at the active or binding site of an enzyme. One of the most common three dimensional structural motifs for peptides in vivo is an a helix. For example, 60% of the segments of proteins around the phosphorylation sites for PKA and PKC kinases display helix motifs. See *J. Mo.l Model*, 11:431-438 (2005). Helix motifs are commonly found in segments of proteins involved in protein-protein interactions or protein-DNA interactions. The a helix structure is also found in transmembrane proteins, proteins involved in fusion processes (gp 41 from HIV), and antimicrobial sequences, among others.

Examination of the protein structures that contain helix motifs has lead to the formulation of general rules for helix folding. See for example, "De Novo design of helix bundles," *J. Mol. Biol.*, 281, 379-391 (1998). Further structural studies of de novo design helix bundles have generated rules for residue location that favor a particular helix-helix association (dimers, trimers, tetramers, etc). See *Protein Science*, 6, 80-88, (1997).

Figure 9:
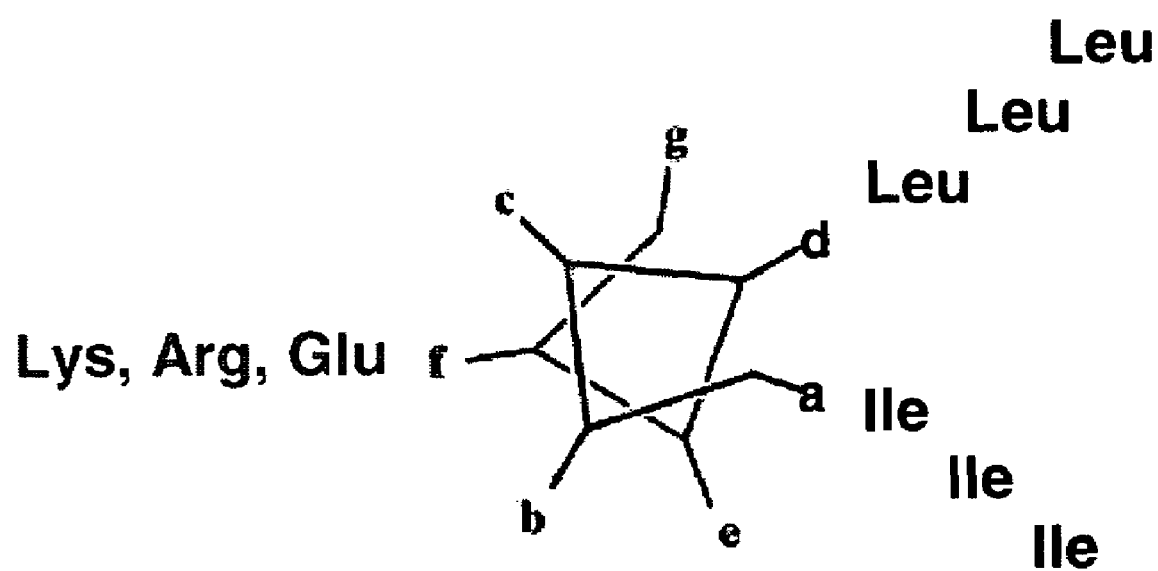
FIG. 9 is a helical wheel diagram of a heptad repeat comprised of exemplary amino acid sequences (a-g) that favor dimeric association and helix formation.

FIG. 9 shows a helical wheel diagram of a heptad repeat having a primary amino acid sequence represented by the letters a through g. The positions occupied by amino acids in the heptad repeat are denoted by the letters a through g. The heptad structure of FIG. 9 comprises amino acids at positions a and d that favor dimeric association, such as through an interhelical hydrophobic layer. Generally, a heptad repeat is a structural motif that consists of a repeating pattern of amino acids. Optionally, the helical structure could contain two, three, or more heptad repeats. In this motif positions a and d are occupied by hydrophobic residues that hold the helix together. Hydrophobic residues comprise, for example, valine (Val), isoleucine (Ile), and leucine (Leu). The remaining amino acid positions, b, c, e, f, and g are typically occupied by hydrophilic amino acids. Since the positions b, c, e, f, and g can be occupied by a variety of amino acids, thousands of different sequences are possible. Preferred amino acids that will be exposed to the solvent are placed at position f. Typically the amino acid at position f is a large hydrophilic residue, such as for example, Lys (lysine), Arg (arginine), or Glu (glutamic acid). In some embodiments the N-terminal residue (amino acid) will be proline (Pro). Proline is the amino acid most frequently found at the beginning of helices and is frequently considered to be a helix initiator. Methods such as for example, those discussed in Lupas, A., Van Dyke, M., and Stock, J., "Predicting Coiled Coils from Protein Sequences," *Science* 252:1162-1164 (1991), can be used to predict whether two sequences will coil and to select sequences that will form coils.

Figure 10:
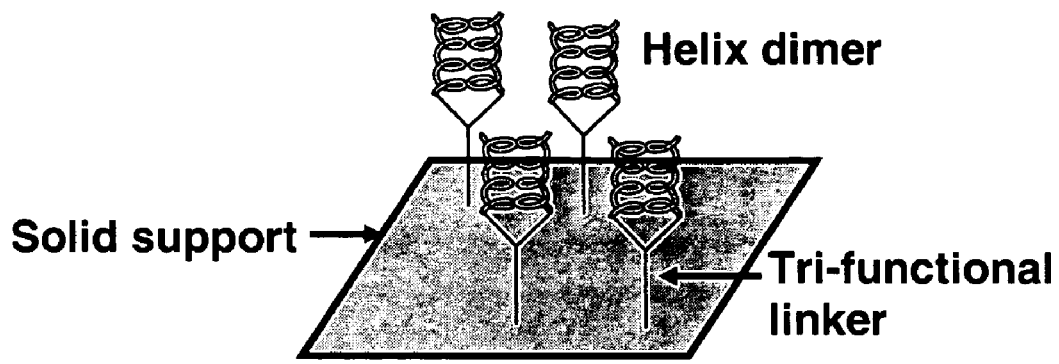
FIG. 10 shows a simplified picture of helix dimers on a solid substrate.

Helixes built from two peptide chains may be created from a branch point created by inserting a bifurcation group into a peptide being synthesized on a solid surface or through the use of a trifunctional linker molecule. In general, a trifunctional linker molecule is a molecule having three functional groups, one capable of attaching to a solid surface or a derivatized solid surface, and two that are capable of coupling to an amino acid or peptide chain. A trifunctional linker molecule typically is a molecule having a molecular weight less than about 300 Daltons. The trifunctional linker molecule allows the synthesis of two peptide chains in close proximity. The trifunctional linker could comprise, for example, a carboxy group for surface attachment and two amino groups upon which to grow peptide chains. Exemplary trifunctional linkers include di-Fmoc or di-Boc protected: lysine, ornithine, diaminopropionic acid, and diaminobutanoic acid. Optionally, a linker molecule may be first attached to the substrate surface and the trifunctional linker attached to the linker molecule. Further, linker molecules may optionally be attached to the arms of the trifunctional linker molecule. FIG. 10 provides a simplified picture of helix dimers that have been synthesized on a solid support. In FIG. 10, a trifunctional linker has been coupled to the support surface and the helix dimer built therefrom.

Arrays of peptides may be built having features that comprise helical peptide dimers and features that comprise peptides that do not form helical dimers. An array could contain as few as one feature or region having peptides that are designed to fold into helixes. Thus, some regions or features of the array may have trifunctional linkers attached to the surface or bifurcation points inserted into growing peptide chains and some regions may not have these features.

EXAMPLE 1

A glass substrate was silanated using a solution of 5% APTES (aminopropyl triethoxy silane) in 95% ethanol. The surface of the substrate was then washed and annealed at about 100° C. for about 1 hour. The substrate was then treated with a 5% solution of DIEA (diisopropyl ethyl amine) in DMF (dimethylformamide). A spacer molecule was then coupled by submerging the surface into a solution of O—(N-Boc-2-aminoethyl)-O'—(N-diglycolyl-2-aminoethyl)hexaethyleneglycol, 0.1 M HOBt, and 0.1 M DIC (diisopropylcarbodiimide) in NMP (N-methyl pyrrolidone) with gentle agitation for about 30 min. After coupling was complete, the surface was washed with NMP. Unreacted amine groups on the surface were capped by treatment with 2% acetic anhydride in DMF solution for about 30 minutes. The surface was then washed with DMF and isopropanol.

A photoresist was prepared by mixing about 2.5% by mass of PMMA, 10% by mass of Bis(4-tert-butylphenyl)iodonium triflate and 10% by mass of isopropyl-9H-thioxanthen-9-one in PGMEA solvent and spin coating the mixture over the amino acid derivatized glass surface for about 60 seconds at 2,000 rpm. The photoresist layer was baked at about 85° C. for about 90 seconds. The resulting photoresist layer had a thickness of about 2 μm.

Acid was generated in the photoresist layer by irradiation of the surface of the substrate with 50 mJ at 365 nm UV light through a mask. The reaction was accelerated by a post exposure bake at about 65° C. for about 60 seconds. After the photogenerated acid deprotection was achieved, the surface of the substrate was rinsed with acetone to strip the photoresist and the surface was dried. The surface was neutralized by treatment in 5% DIEA/DMF for about 5-10 minutes and then washed in DMF.

A trifunctional amino acid (Fmoc-Lys(Fmoc)-OH) was coupled to the surface of the substrate using a 0.1 M solution of Fmoc-Lys(Fmoc)-OH, HOBt, and DIC as above. Fmoc was then removed by treating the surface with 20 piperidine in DMF for 15 min followed by DMF wash. Subsequent rounds of coupling and deprotection were accomplished by repeating the above procedures to generate peptides of a desired length. As a result, an octamer peptide, EIYGEFKK an Src kinase substrate, was synthesized on an APTES surface derivatized with a PEG (polyethylene glycol) spacer. Once the synthesis was completed side chain protecting groups were removed by treating the surface with a solution of TFA/HBr containing pentamethylbenzene and thioanisol as scavengers. Src kinase assay was then performed on the side chain deprotected surface. Phosphorylation detection with ProQ staining showed that the phosphoryl transfer reaction took placed.

EXAMPLE 2

An array of wildtype (SDLHKL) and mutant (AGLHKL) peptide was synthesized on an aminated glass surface with a linker molecule, O—(N-Boc-2-aminoethyl)-O'—(N-diglycolyl-2-aminoethyl)hexaethyleneglycol, for spacing the peptides from the surface. The peptides were synthesized in a checkerboard pattern using uniform photodeprotection of t-Boc protecting groups through an open grid mask till the second leucine and spatially localized deprotection through a checkerboard mask for the last two amino acid couplings.

The photodeprotection and coupling of linker molecules and amino acids was carried out as described in Example 1.

The peptide array was incubated for 1 hour with 5 μg/ml monoclonal antibody known to specifically recognize the SDLHKL epitope of human p53 protein. A second incubation was performed with fluorescein-labeled rabbit antibody raised against mouse antibody at a 1:100 dilution in phosphate buffered saline with 0.05% Tween 20. A fluorescent checker board pattern was detected on fluorescence scanning of the array suggesting specific interaction of antibody with the wildtype sequence.

EXAMPLE 3

Photoresist formulations may include a sensitizer in addition to the photogenerated acid catalyst to generate the acid deprotection catalysts. In general, the amount of PMMA in the resist in these exemplary formulations may vary between about 3% and about 50%.

Useful photoresists may be made using diaryliodonium salts (DAI) and photosensitizers. The mass ration between DAI and photosensitizer may be between about 1:10 and 1:1. For instance, (tolylcumyl)polonium tetrakis (pentafluorophenyl)borate with isopropyl-9H-thioxanthen-9-one may be formulated in a 1:10 or 1:1 (or a ratio there between) in PMMA and PGMEA to form final concentrations of between about 0.5% to 10% by mass DAI. The formulation selected may be spun coated on the substrate surface and baked. The radiation exposure dose may be between about 0.02 J and about 10 J. Post exposure baking may be conducted for about 30 to 60 seconds at about 40° C. to about 85° C.

What is claimed is:

1. An array of polymers attached to a substrate wherein the array comprises a support structure having a surface, wherein the surface has a plurality of features, wherein each of the features comprises a plurality of peptides of known sequence attached to the substrate surface, wherein the sequence of peptides in a first feature of the array is different from the sequence of peptides in a second feature of the array, wherein at least one feature of the array comprises a first peptide and a second peptide attached to the surface of the support structure through a bifurcation molecule or a trifunctional linker molecule, and wherein the first and second peptide are capable of forming a helical structure, and wherein the bifurcation molecule or the trifunctional linker molecule is attached to the first and to the second peptide.

2. The array of claim 1 wherein the area occupied by a feature of the array is less than 1mm$^2$.

3. The array of claim 1 wherein an area occupied by a feature of the array is less than 100 μm$^2$.

4. The array of claim 1 wherein the array comprises 1,000 to 10,000 features.

5. The array of claim 1 wherein the substrate is selected from the group consisting of glass, silicon, and silicon having a SiO$_2$ layer.

6. The array of claim 1 wherein the first peptide capable of forming a helical structure comprises between 6 and 25 amino acids.

7. The array of claim 1 wherein the first peptide capable of forming a helical structure comprises one or more heptad repeats.

8. The array of claim 1 wherein the peptides capable of forming a helical structure are attached to the substrate surface through a trifunctional linker and wherein the trifunctional linker is selected from the group consisting of diaminopropionic acid, diaminobutanoic acid, ornithine, and lysine.

9. The array of claim 1 wherein the peptides capable of forming a helical structure are attached to the substrate surface through a bifurcation molecule.

10. An object comprising a substrate having a surface wherein a polymer is attached to the substrate surface, wherein the polymer is comprised of a first and a second peptide and the first and the second peptides are attached to the substrate through a single bifurcation molecule or a trifunctional linker molecule and wherein the first and the second peptides are capable of forming a helical structure, and wherein the bifurcation molecule or the trifunctional linker molecule is attached to the first and to the second peptide.

11. The object of claim 10 wherein the substrate is selected from the group consisting of glass, a bio-compatible polymer, silicon, and silicon having a SiO$_2$ layer.

12. The object of claim 10 wherein the first peptide capable of forming a helical structure comprises between 6 and 25 amino acids.

13. The object of claim 10 wherein the first peptide capable of forming a helical structure comprises one or more heptad repeats.

14. The object of claim 10 wherein the peptides capable of forming a helical structure are attached to the substrate surface through a trifunctional linker.

15. The object of claim 10 wherein the trifunctional linker is selected from the group consisting of diaminopropionic acid, diaminobutanoic acid, ornithine, and lysine.

16. The object of claim 10 wherein the peptides capable of forming a helical structure are attached to the substrate surface through a bifurcation molecule.

* * * * *